US00PP08884P

United States Patent [19]

Van der Jagt

[11] Patent Number: Plant 8,884

[45] Date of Patent: Sep. 6, 1994

[54] CHRYSANTHEMUM NAMED YELLOW REAGAN

[75] Inventor: Martinus Van der Jagt, Langeraar, Netherlands

[73] Assignee: Chrysanthemum Breeders Association, N.V., Netherlands Antilles

[21] Appl. No.: 92,943

[22] Filed: Jul. 19, 1993

Related U.S. Application Data

[63] Continuation of Ser. No. 767,881, Sep. 30, 1991, abandoned.

[30] Foreign Application Priority Data

Oct. 2, 1990 [NL] Netherlands ..... CHR1866

[51] Int. Cl.[5] ..... A01H 5/00

[52] U.S. Cl. ..... Plt./82.2

[58] Field of Search ..... Plt. 82.2

[56] References Cited

PUBLICATIONS

Datta, 1991, "Evaluation of recurrent irradiation on vegetatively propagated ornmanetals: Chrysanthemum", J. Nuclear Agric. Biol., 20(2):81–86.

Banerji, et al., 1990, "Induction of somatic mutation in chrysanthemum cultivar 'Anupam'", J. Nuclear Agric. Biol., 19:252–256.

"Mutation studies on chrysanthemum", NBRI Newsletter, 1989, 16(1):2–3.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Gupta, et al., 1978, "Mutation breeding of Chrysanthemum. II. Detection of gamma ray induced mutations in vM2", J. Nuclear Agric. Biol., 7(2):50-54.

Das, et al., 1977, "Improvement of some vegetatively propagated ornamentals by gamma radiation", Indian J. Hort. 34(2):169–174.

Searle, et al., 1968, "Chrysanthemum the Year Round", Blanford Press, London, pp. 27–29, 320–327.

Broertjes, 1966, "Mutation breeding of chrysanthemums", Euphytica, 15:156–162.

Dowrick, et al., 1966, "The induction of mutation in chrysanthemum using X- and gamma radiation", Euphytica, 15:204–210.

*Primary Examiner*—Howard J. Locker

*Attorney, Agent, or Firm*—Parkhurst, Wendel & Rossi

[57] ABSTRACT

A new and distinct cultivar of Chrysantheum plant named Yellow Reagan, bearing medium sized yellow blooms with a center and performance of 24–28 days.

2 Drawing Sheets

This is a continuation of application Ser. No. 07/767,881, filed Sep. 30, 1991, now abandoned. The present application is related to the following copending applications:

| Application No. | Filing Date | Title |
|---|---|---|
| 07/780,305 (now U.S. Plant Pat. No. 8,642) | October 22, 1991 | Reagan |
| 07/780,237 | October 22, 1991 | Orange Reagan |
| 08/088,104 | July 8, 1993 | Dark Reagan |
| 08/101,275 | August 2, 1993 | Coral Reagan |
| 08/092,942 | July 19, 1993 | Sulfur Reagan |
| 08/092,941 | July 19, 1993 | Bronze Reagan |
| 08/088,107 | July 8, 1993 | White Reagan |
| 08/101,278 | August 2, 1993 | Salmon Reagan |

BACKGROUND OF THE INVENTION

The present invention comprises a new and distinct cultivar of Chrysanthemum plant which is a naturally occurring sport of a chrysanthemum named Reagan, which in turn is a cross of unknown *Chrysanthemum morifolium* parents. The Chrysanthemum named Reagan is described in co-pending U.S. patent application Ser. No. 07/780,305 now U.S. Plant Pat. No. 8,642. The new cultivar was discovered as a whole plant mutation in 1990 in a greenhouse in Holland.

The invention has been asexually reproduced by cuttings at the same location. The new cultivar has been found to retain all of its distinctive characteristics through successive asexual propagations.

SUMMARY OF THE INVENTION

The present invention is a new and distinct variety of Chrysanthemum of a medium sized bloom and yellow color.

BRIEF DESCRIPTION OF THE DRAWINGS

The present invention of a new and distinct variety of Chrysanthemum is shown in the accompanying drawings, the color being as nearly true as possible with color photographs of this type.

FIG. 1 shows the full bloom of the new cultivar.

FIG. 2 shows various stages of bloom of the new cultivar.

FIG. 3 shows foliage and petiole of the new cultivar.

DESCRIPTION OF THE INVENTION

This new variety of Chrysanthemum is of the botanical classification *Chrysanthemum morifolium.* When grown in the vicinity of Ter Aar, Holland, it has a response time of approximately 7½ weeks. This new variety produces medium sized yellow blooms with a green center having a 4 week performance (i.e., vase life of 24–28 days). This new variety of chrysanthemum has been found to retain its distinctive characteristics throughout successive propagations and may be planted under greenhouse conditions in Holland between weeks 50 and 35 (i.e., between December 1 and August 30).

The following is a description of the plant and characteristics (color designations are from R.H.S. Colour Chart) that distinguish it over related known varieties and its antecedents:

Botanical classification: *Chrysanthemum morifolium.*

Bud:

- Size.—Medium (cross section ±1.0 cm, height ±0.7 cm).
- *Form.*—Round and flat.
- *Outside color.*—Yellow 9C.

Bloom:

- *Size.*—Medium.
- *Fully expanded.*—6½–7 cm.
- *Borne.*—Upper portion, single flower per peduncle; Lower portion, plural flowers per peduncle.
- *Stems.*—Strong, thick.
- *Form.*—Single (daisy).
- *Performance.*—Very good 24–28 days (18°–20°C.).

Color:

- *Center of flower.*—Immature: Yellow Green 151C. Mature: Yellow Green 154A.
- *Base of petals.*—Yellow 5C.
- *Inside of petals.*—Yellow 5C.
- *Reverse of petals.*—Yellow 4C.
- *Outer petals.*—Yellow 5C.
- *Tonality from a distance.*—A yellow daisy with a fresh looking center having little or no pollen.
- *Discoloration.*—Some to Yellow 8B.
- *Pollen.*—Yellow-Orange 14A.

Petals:

- *Texture.*—Upperside smooth, Underside smooth.
- *Number.*—24–30 (two rows).
- *Cross-section.*—Flat, two keels.
- *Arrangement.*—Imbricated.
- *Persistence.*—Good. Petals keep straight or reflex somewhat at the edge at the end of blooming.
- *Fragrance.*—Typical Chrysanthemum.
- *Disc diameter.*—1.5 cm.

Reproductive organs:

- *Stamen.*—Yellow, thick 3 mm in length.
- *Pollen.*—Appears at the late stage of blooming, yellow-orange in color.
- *Styles.*—Green, thick. Length: ±5 mm.
- *Stigmas.*—Yellow. Width: ±1 mm.
- *Ovaries.*—Enclosed in calyx.

Plant:

- *Form.*—Spray mum meant for erect culture. Herbaceous.
- *Growth.*—Strong.
- *Height.*—100–125 cm.
- *Peduncle.*—Near the top ±14 cm, Near the middle ±24 cm, Near the bottom ±28 cm.
- *Internodes.*—3 cm.
- *Flowering response.*—7½ weeks.

Foliage:

- *Color.*—Upperside Green 137 A, Underside 137 C.
- *Size.*—Length ±12 cm, Width ±9 cm.
- *Quantity.*—22–28.
- *Shape.*—Lobed, see photograph.
- *Texture.*—Upperside rough, Underside smooth. Slightly hirsute.
- *Ribs and veins.*—Ribs well developed, Veins not so developed.
- *Edge.*—Crenated.

Distinguising characteristics of the Chrysanthemums of the Reagan family are summarized below in Tables IA and IB. The color designations in the Tables are from The R.H.S. Colour Chart.

TABLE IA

| TITLE | REAGAN | WHITE REAGAN |
|---|---|---|
| BUD OUTSIDE COLOR | GREYED-PURPLE 186D BUT PALER | YELLOW 4D |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | PURPLE 75B | WHITE 155D BUT WHITER AND BRIGHTER |
| INSIDE OF PETALS | PURPLE 75B | WHITE 155D BUT WHITER AND BRIGHTER |
| REVERSE OF PETALS | RED-PURPLE 69A BUT PALER | WHITE 155D BUT WHITER AND BRIGHTER |
| OUTER PETALS | PURPLE 75B | WHITE 155D BUT WHITER AND BRIGHTER |
| PETAL CROSS-SECTION | FLAT | FLAT |

| TITLE | CORAL REAGAN | DARK REAGAN |
|---|---|---|
| BUD OUTSIDE COLOR | GREYED-PURPLE 186A | BETWEEN GREYED PURPLE 186A AND B |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | GREYED-RED 179C BUT REDDER | RED-PURPLE 69B LIGHTLY OVERLAID WITH RED-PURPLE 72A GIVING AN OVERALL IMPRESSION OF PURPLE 75A BUT PINKER |
| INSIDE OF PETALS | GREYED-RED 179C BUT REDDER | RED-PURPLE 69B LIGHTLY OVERLAID WITH RED-PURPLE 72A GIVING AN OVERALL IMPRESSION OF PURPLE 75A BUT PINKER |
| REVERSE OF PETALS | GREYED-YELLOW 162D TINGED WITH RED-PURPLE 71B BETWEEN RIBS AND MARGIN | RED-PURPLE 69C WITH A LIGHT TESSELLATION OF RED-PURPLE 72A |
| OUTER PETALS | GREYED-RED 179C BUT REDDER | RED-PURPLE 69B LIGHTLY OVERLAID WITH RED-PURPLE 72A GIVING AN OVERALL IMPRESSION OF PURPLE 75A BUT PINKER |
| PETAL CROSS-SECTION | FLAT | CONVEX |

| TITLE | ORANGE REAGAN | BRONZE REAGAN |
|---|---|---|
| BUD OUTSIDE COLOR | GREYED-RED 180A | GREYED-RED 179C |
| CENTER OF FLOWER | | |

TABLE IA-continued

| | | |
|---|---|---|
| IMMATURE: | YELLOW-GREEN 151C | YELLOW-GREEN 151C |
| MATURE: | YELLOW-GREEN 154A | YELLOW-GREEN 154A |
| BASE OF PETALS | BETWEEN GREYED ORANGE 169A AND B | YELLOW 8A WITH AN OVERLAY OF GREYED RED 179B |
| INSIDE OF PETALS | BETWEEN GREYED ORANGE 169A AND B | YELLOW 8A WITH AN OVERLAY OF GREYED RED 179B |
| REVERSE OF PETALS | NEAREST TO GREYED-ORANGE 163B TINGED WITH RED BETWEEN THE RIBS | YELLOW 8C TINGED ALONG THE CENTER WITH GREYED RED 179B IN A TESSELATED PATTERN |
| OUTER PETALS | BETWEEN GREYED-ORANGE 169A AND B | YELLOW 8A WITH AN OVERLAY OF GREYED RED 179B |
| PETAL CROSS-SECTION | CONVEX | FLAT |

| TITLE | YELLOW REAGAN | SULPHUR REAGAN |
|---|---|---|
| BUD OUTSIDE COLOR | YELLOW 9C | YELLOW 10C |
| CENTER OF FLOWER | | |
| IMMATURE: | YELLOW-GREEN 151C | YELLOW-GREEN 151C |
| MATURE: | YELLOW-GREEN 154A | YELLOW-GREEN 154A |
| BASE OF PETALS | YELLOW 5C | YELLOW 6D |
| INSIDE OF PETALS | YELLOW 5C | YELLOW 6D |
| REVERSE OF PETALS | YELLOW 4C | YELLOW 6D |
| OUTER PETALS | YELLOW 5C | YELLOW 6D |
| PETAL CROSS-SECTION | FLAT | FLAT |

| TITLE | SALMON REAGAN |
|---|---|
| BUD OUTSIDE COLOR | NEAREST TO YELLOW-ORANGE 23D |
| CENTER OF FLOWER | |
| IMMATURE: | YELLOW-GREEN 151C |
| MATURE: | YELLOW-GREEN 154A |
| BASE OF PETALS | NEAREST TO ORANGE 29C |
| INSIDE OF PETALS | NEAREST TO ORANGE 29C |
| REVERSE OF PETALS | NEAREST TO YELLOW-ORANGE 22D |
| OUTER PETALS | NEAREST TO ORANGE 29C |
| PETAL CROSS-SECTION | FLAT |

TABLE IB

| TITLE | REAGAN | WHITE REAGAN |
|---|---|---|
| STEM INFORMATION | | |
| STEM: GREEN COLOR | YELLOW-GREEN 144A | NEAREST GREEN 143C |
| STEM: ANTHOCYANIN COLORATION | ABSENT | ABSENT |
| STEM: STRENGTH | MEDIUM | MEDIUM TO STRONG |
| STEM: BRITTLENESS | PRESENT | PRESENT |
| PEDUNCLE INFORMATION | | |
| LATERAL SHOOT: ATTACHMENT TO STEM | MEDIUM | WEAK TO MEDIUM |
| LATERAL SHOOT: ANGLE BETWEEN LATERAL SHOOT AND STEM | MEDIUM | MEDIUM |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | ROUNDED | ASYMMETRIC |
| LEAF: APEX | CUSPIDATE | MUCRONATE |
| GROWTH: DIFFERENCE IN AVERAGE LENGTH (IN CMS) | 0 | 0 |
| RESPONSE TIME: DIFFERENCE IN DAYS OF AVERAGE RESPONSE | 0 | 0 |
| RESPONSE OF ALAR: DOSE THAT HAS TO BE USED TO GET AN AVERAGE LENGTH OF ABOUT 90 CMS (DOSE IN GRAMS PER 100 LITER OF WATER) | 300 | 300 |
| YEAR OF DISCOVERY | 1986 | 1989 |

TABLE IB-continued

| TITLE | CORAL REAGAN | DARK REAGAN |
|---|---|---|
| STEM INFORMATION | | |
| STEM: GREEN COLOR | YELLOW-GREEN 144A | YELLOW-GREEN 144A |
| STEM: ANTHOCYANIN COLORATION | PRESENT | PRESENT |
| STEM: STRENGTH | MEDIUM | MEDIUM |
| STEM: BRITTLENESS | ABSENT | PRESENT |
| PEDUNCLE INFORMATION | | |
| LATERAL SHOOT: ATTACHMENT TO STEM | WEAK TO MEDIUM | MEDIUM |
| LATERAL SHOOT: ANGLE BETWEEN LATERAL SHOOT AND STEM | SMALL | MEDIUM |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | ASYMMETRIC | ASYMMETRIC |
| LEAF: APEX | CUSPIDATE | MUCRONATE |
| GROWTH: DIFFERENCE IN AVERAGE LENGTH (IN CMS) | −5 | 0 |
| RESPONSE TIME: DIFFERENCE IN DAYS OF AVERAGE RESPONSE | +1 | +½ |
| RESPONSE OF ALAR: DOSE THAT HAS TO BE USED TO GET AN AVERAGE LENGTH OF ABOUT 90 CMS | | |

TABLE IB-continued

| | | |
|---|---|---|
| (DOSE IN GRAMS PER 100 LITER OF WATER) | | |
| | 250 | 300 |
| YEAR OF DISCOVERY | 1988 | 1988 |
| TITLE | ORANGE REAGAN | BRONZE REAGAN |
| STEM INFORMATION | | |
| STEM: GREEN COLOR | BETWEEN YELLOW-GREEN 144A AND 146B | YELLOW-GREEN 144A |
| STEM: ANTHOCYANIN COLORATION | PRESENT | PRESENT |
| STEM: STRENGTH | MEDIUM | MEDIUM |
| STEM: BRITTLENESS | PRESENT | ABSENT |
| PEDUNCLE INFORMATION | | |
| LATERAL SHOOT: ATTACHMENT TO STEM | MEDIUM | WEAK |
| LATERAL SHOOT: ANGLE BETWEEN LATERAL SHOOT AND STEM | SMALL | SMALL |
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | CONVERGING | CONVERGING |
| LEAF: SHAPE OF BASE | TRUNCATE | ASYMMETRIC |
| LEAF: APEX | CUSPIDATE | CUSPIDATE |
| GROWTH: DIFFERENCE IN AVERAGE LENGTH (IN CMS) | +10 | 0 |
| RESPONSE TIME: DIFFERENCE IN DAYS OF AVERAGE RESPONSE | −1 | −½ |
| RESPONSE OF ALAR: DOSE THAT HAS TO BE USED TO GET AN AVERAGE LENGTH OF ABOUT 90 CMS (DOSE IN GRAMS PER 100 LITER OF WATER) | 450 | 250 |
| YEAR OF DISCOVERY | 1988 | 1988 |
| TITLE | YELLOW REAGAN | SULPHUR REAGAN |
| STEM INFORMATION | | |
| STEM: GREEN COLOR | YELLOW-GREEN 146B | NEAREST 143C |
| STEM: ANTHOCYANIN COLORATION | ABSENT | ABSENT |
| STEM: STRENGTH | MEDIUM | MEDIUM TO STRONG |
| STEM: BRITTLENESS | ABSENT | ABSENT |
| PEDUNCLE INFORMATION | | |
| LATERAL SHOOT: ATTACHMENT TO STEM | WEAK TO MEDIUM | WEAK TO MEDIUM |
| LATERAL SHOOT: ANGLE BETWEEN LATERAL SHOOT AND STEM | SMALL | SMALL |

TABLE IB-continued

| | | |
|---|---|---|
| ADDITIONAL FOLIAGE INFORMATION | | |
| LEAF: SHAPE OF BASE OF SINUS BETWEEN LATERAL LOBES | ROUND | ROUND |
| LEAF: MARGINS OF SINUS BETWEEN LATERAL LOBES | PARALLEL | PARALLEL |
| LEAF: SHAPE OF BASE | ASYMMETRIC | ASYMMETRIC |
| LEAF: APEX | MUCRONATE | MUCRONATE |
| GROWTH: DIFFERENCE IN AVERAGE LENGTH (IN CMS) | 0 | +10 |
| RESPONSE TIME: DIFFERENCE IN DAYS OF AVERAGE RESPONSE | +1 | −1 |
| RESPONSE OF ALAR: DOSE THAT HAS TO BE USED TO GET AN AVERAGE LENGTH OF ABOUT 90 CMS (DOSE IN GRAMS PER 100 LITER OF WATER) | 280 | 450 |
| YEAR OF DISCOVERY | 1990 | 1990 |
| TITLE | SALMON REAGAN | |
| STEM INFORMATION | | |
| STEM: GREEN COLOR | YELLOW-GREEN 144A | |
| STEM: ANTHOCYANIN COLORATION | PRESENT | |
| STEM: STRENGTH | MEDIUM | |
| STEM: BRITTLENESS | PRESENT | |
| PEDUNCLE INFORMATION | | |
| LATERAL SHOOT: ATTACHMENT TO STEM | MEDIUM | |
| LATERAL SHOOT: ANGLE BETWEEN LATERAL SHOOT AND STEM | MEDIUM | |
| ADDITIONAL FOLIAGE INFORMATION | | |
| LEAF: SHAPE OF BASE OF SINUS BETWEEN LATERAL LOBES | ROUND | |
| LEAF: MARGINS OF SINUS BETWEEN LATERAL LOBES | PARALLEL | |
| LEAF: SHAPE OF BASE | ASYMMETRIC | |
| LEAF: APEX | CUSPIDATE | |
| GROWTH: DIFFERENCE IN AVERAGE LENGTH (IN CMS) | +10 | |
| RESPONSE TIME: DIFFERENCE IN DAYS OF AVERAGE RESPONSE | 0 | |
| RESPONSE OF ALAR: DOSE THAT HAS TO BE USED TO GET AN AVERAGE LENGTH OF ABOUT 90 CMS (DOSE IN GRAMS PER 100 LITER OF WATER) | 350 | |
| YEAR OF DISCOVERY | 1987 | |

I claim:

1. A new and distinctive variety of Chrysanthemum plant as described and illustrated.

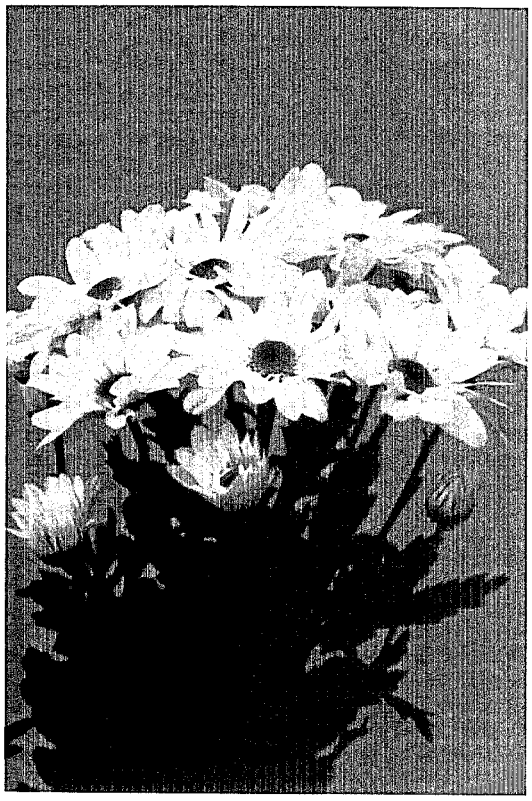

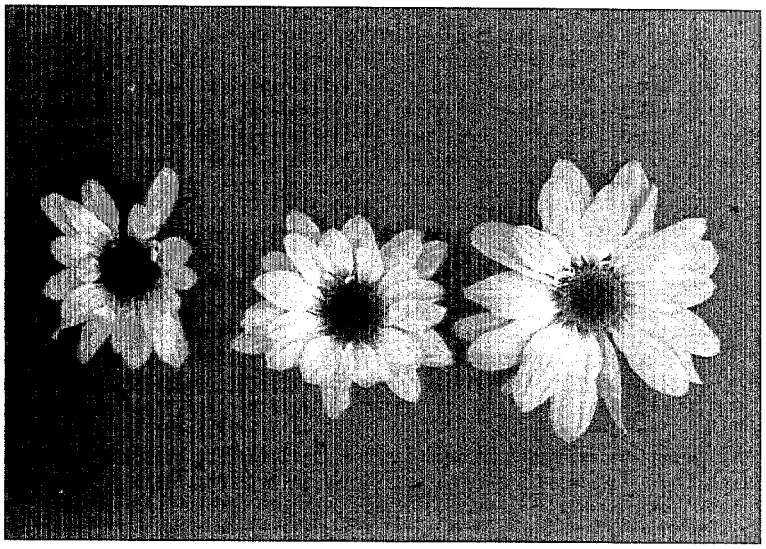
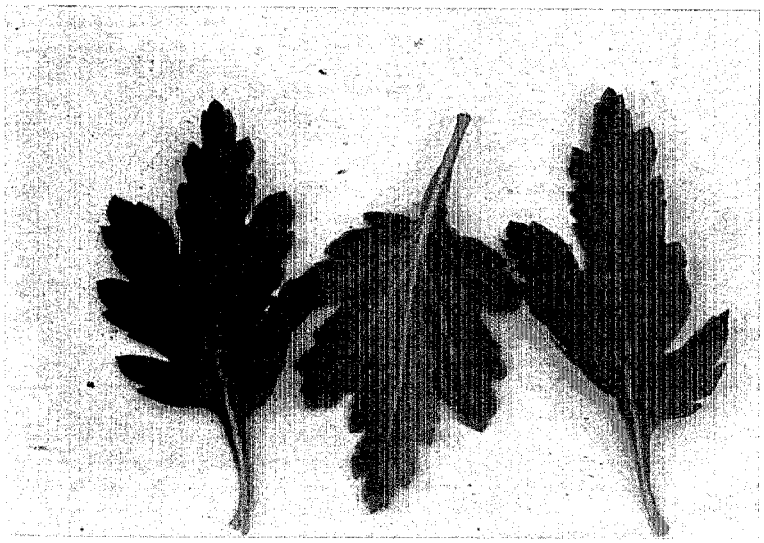

* * * * *